United States Patent [19]

Mes-Masson et al.

[11] Patent Number: 5,710,038
[45] Date of Patent: Jan. 20, 1998

[54] PRIMARY CULTURES OF NORMAL AND TUMORAL HUMAN OVARIAN EPITHELIUM

[75] Inventors: Anne-Marie Mes-Masson, Dollard-des-Ormeaux; Diane Provencher, St-Basile Le Grand, both of Canada

[73] Assignee: Universite De Montreal, Montreal, Canada

[21] Appl. No.: 344,960

[22] Filed: Nov. 25, 1994

[51] Int. Cl.$^6$ .................................................... C12N 5/00
[52] U.S. Cl. .................................. 435/240.2; 435/240.21
[58] Field of Search ............................ 435/240.2, 240.1, 435/240.21

[56] References Cited

PUBLICATIONS

Tsoa et al., Experimental Cell Research, 218(2):499–507 (1995).
Lounis et al., Experimental Cell Research, 215(2):303–09 (Dec. 1994).
Auersperg et al., Laboratory Investigation, 71(4):510–18 (Oct. 1994).
Hirte et al., Cancer, 74(3):900–06 (Aug. 1994).
Karlan et al., Gynecologic Oncology, 31(1): 103–12 (1988).
Ishiwata et al., Gynecologic Oncology, 26(3):340–54 (1987).
Vigani et al., Boll. Soc. Ital. Biol. Sper., 66(6):537–42 (1990).
Hills et al., Br. J. Cancer, 59(4):527–34 (1989).
Berkowitz et al., Am. J. Obstet. Gynecol., 146(6):607–12 (1983).
Hirte et al., Proc. Annu. Meet. Am. Assoc. Cancer Res., 34:A219 (1993).
Emons et al, Cancer Research, 53(22):5439–46 (1993).
Maines–Bandiera et al., Biology of Reproduction, 44(Suppl 1), Paper No. 253 (1991).
ATCC Catalogue of Cell Lines & Hybridomas, 7th edition, pp. 148, 238, 243–245, and 272 (1992).
Scully, 1977, Ovarian Tumors—A Review, Am. J. Pathol. 87: 686–720.
Provencher et al., 1993, Gyn. Oncol. 50: 78–83.
Davies et al., 1993, Cancer Res. 53: 2087–2091.
Khokha et al., 1989, Science 243: 947–950.
Ponton et al., 1991, Cancer Res. 51: 2138–2143.
Siemens et al., 1988, J. Cell Physiol. 134:347–351.
Kruk et al. 1990, Lab. Inves. 63: 132–136.
Wigler et al., 1978, Cell 14: 725–731.
Ganly et al., 1991, Nucleic Acids Res. 19: 3757.
Ganly et al., 1991, Nucleic Acids Res. 19: 3760.
Ganly et al., 1992, Genomics 12: 221–228.
Gareau et al., 1988, Nucleic Acids Res. 16: 1223.
Orita et al., 1989, Genomics 5: 874–879.
Ehlen and Dubeau 1990, Oncogene 5: 219–223.
Zheng et al., 1991, Cancer Res. 51: 4045–4051.
Houle et al., 1991, Genes, Chromosomes and Cancer 3: 358–366.
Krueger et al., 1990, EMBO J. 9: 3241–3252.
Latif et al., 1993, Science 260: 1317–1320.
Unemori et al., 1986, J. Cell. Biol. 103: 1021–1031.

*Primary Examiner*—David M. Naff
*Assistant Examiner*—S. Saucier
*Attorney, Agent, or Firm*—Klauber & Jackson

[57] ABSTRACT

The present invention relates to primary cultures or established cell lines of ovarian epithelium origin which are substantially equivalent to the cells from the original clinical material from which they are derived and can serve as a powerful model in numerous types of studies including the elaboration of a patient-based tumor profile, thereby permitting a more precise and personalized design of an efficacious therapeutic regimen for cancer therapy. The invention further relates to a method to derive primary cell cultures from benign and malignant ovarian tissue and from ascites.

8 Claims, 5 Drawing Sheets

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="DNA"

( x i ) SEQUENCE DESCRIPTION: SEQ ID NO:1:

TATCTGTTCA CTTGTGCCCT CAC      23

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="dna"

( x i ) SEQUENCE DESCRIPTION: SEQ ID NO:2:

CCACTCGGAT AAGATGCTGA GGA      23

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="DNA"

( x i ) SEQUENCE DESCRIPTION: SEQ ID NO:3:

AAGGCGCACT GGCCTCATC      19

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="DNA"

( x i ) SEQUENCE DESCRIPTION: SEQ ID NO:4:

AGTGTGCAGG GTGGCAAGTG G      21

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="DNA"

( x i ) SEQUENCE DESCRIPTION: SEQ ID NO:5:

ACGTTAGTGG CTCATATGAC                                           20

( 2 ) INFORMATION FOR SEQ ID NO:6:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc ="DNA"

( x i ) SEQUENCE DESCRIPTION: SEQ ID NO:6:

TCATTCGAGT TAGTGCAAAG                                           20

( 2 ) INFORMATION FOR SEQ ID NO:7:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc ="DNA"

( x i ) SEQUENCE DESCRIPTION: SEQ ID NO:7:

AACGTTGGAC CTCAAGCCCA T                                         21

( 2 ) INFORMATION FOR SEQ ID NO:8:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc ="DNA"

( x i ) SEQUENCE DESCRIPTION: SEQ ID NO:8:

CAGGGTTCCT TCTATAAACA TG                                        22

( 2 ) INFORMATION FOR SEQ ID NO:9:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc ="DNA"

( x i ) SEQUENCE DESCRIPTION: SEQ ID NO:9:

AAAGACTTCC TTCTGAGATG GG                                        22

( 2 ) INFORMATION FOR SEQ ID NO:10:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear -continued (i i) MOLECULE TYPE: other nucleic acid
    (A) DESCRIPTION: /desc ="DNA"

(x i) SEQUENCE DESCRIPTION: SEQ ID NO:10:

CAGTCTGCTG TGGTTTCAGT CT    22

(2) INFORMATION FOR SEQ ID NO:11:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc ="DNA"

(x i) SEQUENCE DESCRIPTION: SEQ ID NO:11:

CTTTACCAGG AAAAGACTCT A    21

(2) INFORMATION FOR SEQ ID NO:12:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc ="DNA"

(x i) SEQUENCE DESCRIPTION: SEQ ID NO:12:

TGCTGTCTAT TACAATATAG G    21

(2) INFORMATION FOR SEQ ID NO:13:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc ="DNA"

(x i) SEQUENCE DESCRIPTION: SEQ ID NO:13:

CACAGCTACC GAGGTCACCT T    21

(2) INFORMATION FOR SEQ ID NO:14:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc ="DNA"

(x i) SEQUENCE DESCRIPTION: SEQ ID NO:14:

ATACTTCTCT AATGGGCAGG C    21

PRIMARY CULTURES OF NORMAL AND TUMORAL HUMAN OVARIAN EPITHELIUM

BACKGROUND OF THE INVENTION

1. Field of the Invention

The invention relates to primary cell cultures and cell lines derived from normal ovaries, from benign or malignant ovarian tissue and from ascites. These primary cell cultures are substantially equivalent to the cells from the original clinical material from which they derive, and can provide a powerful model system for the study of ovarian epithelium under normal and pathological conditions.

The invention further relates to a method to derive primary cell cultures from benign and malignant ovarian tissue and from ascites.

2. Description of the Prior Art

The ovary is a complex organ consisting of a heterogeneous population of cells programmed for distinct functions. All epithelial ovarian tumors originate from either the surface epithelium or from the crypts or inclusion cysts covered by this surface epithelium. Epithelial ovarian tumors are histologically heterogeneous and have been classified according to their cell type, in seven (7) different histological groups (Scully, 1977, Ovarian Tumours-A Review, Am. J. Pathol. 87: 686–720). Ovarian tumors are also graded according to their degree of differentiation: borderline or low malignant potential represent minimal deviation from their benign counterpart while well differentiated tumors are grade I, moderately differentiated tumors are grade II, and poorly differentiated tumors are grade III carcinomas.

After breaching the ovarian capsule through their inventive potential, the most common behavior of ovarian cancer is to seed the peritoneal fluid leading to subsequent implantation over peritoneal surfaces with ascites formation. Present in at least one third of all cases, fresh ascites is in fact a voluminous exudate with a cellular fraction consisting mainly of ovarian epithelial cells that share antigenic cell-surface markers similar to their solid tumor counterpart and some lymphocyte and mesothelial cell infiltration (Provencher et al., 1993, Gyn. Oncol. 50: 78–83). In ovarian cancer, metastases are largely confined to the peritoneal cavity, and death is usually due to the bulk of tumor contained in this area. Thus, in ovarian cancer, as in numerous types of cancer, the principal cause of mortality is not the primary tumor but metastases which are secondary tumors formed at sites removed from the original lesion. Since ovarian cancers are often diagnosed late in the disease process, cancer cells have generally spread to extraovarian sites.

Metastasis normally requires the proteolytic breakdown of the main components of support structures. This proteolytic degradation involves metallo-proteinases. The role of metalloproteinases in several diseases involving tissue degradation, promotion of wound healing and tumor progression, has prompted interest in the therapeutic potential, provided by metalloproteinase inhibitors. It was shown that a synthetic inhibitor, which inhibits a broad spectrum of metalloproteinases, decreased tumor burden, resolved ascitic disease and increased survival of treated nude mice harboring human ovarian carcinoma xenographs (Davies et al. ,1993, Cancer Res. 53: 2087–2091). In vivo, metalloproteinases are down-regulated by specific inhibitors, such as the tissue inhibitors of metalloproteinases (TIMPs). Studies have shown an inverse correlation between TIMP-1 levels and the invasive potential of murine and human tumor cells (Khokha et al., 1989, Science 243: 947–950; and Ponton et al., 1991, Cancer Res. 51: 2138 –2143). Thus, an assessment of the level of TIMP-1 in ovarian cancer cells, could provide important informations as to their invasion potential. Furthermore, the maintenance of relatively high levels of TIMP-1 in the ovarian cancer cells could ensure a better prognosis for the patient.

While epithelial ovarian cancer is the second most common gynecological cancer, it is the most lethal, accounting for nearly half of the deaths associated with gynecological pelvic malignancies. Ovarian cancer is also the fifth leading cause of cancer-related deaths in women, following breast, lungs, colon and pancreatic cancer. The present methodology for ovarian cancer treatment usually involves surgery and/or radiotherapy and/or chemotherapy. The choice of the right chemotherapeutic agent, to which the cancer cells will respond, is based on trial and error. It would thus be immensely useful to clinicians to know in advance to which kind of treatment the cancer cells are sensitive, so as to more precisely direct the therapy.

In spite of the fact that ovarian surface epithelium (OSE) -derived carcinomas are the most frequent cause of gynecological cancer deaths, studies to define the cellular and molecular events associated with this cancer have been hampered by the lack of a suitable model.

The number of cell lines available to study ovarian cancer at the molecular level is low and does not reflect the histological diversity of ovarian cancer. Presently, the cell lines available are: i) two (2) ovarian-primary cell lines (Caov-3 [ATCC HTB 75; American Type Culture Collection, 12301 Parklawn Drive, Rockville, Md. 20852], an adenocarcinoma and SW626 [ATCC HTB 78], a cystadenocarcinoma); ii) three (3) ovarian ascites cell lines (NIHOVCAR-3 [ATCC HTB 161]and SKOV-3 [ATCC HTB 77], both adenocarcinomas, and PA-1 [ATCC CRL 1571], a teratocarcinoma); iii) an ovarian-metastasis cell line (Caov-4; ATCC HTB 76); and iv) a non ovarian metastasis derived from Burkitt tumors of the ovary (EB-2; ATCC HTB 61). Importantly, these commercially available cell lines do not always demonstrate the same properties as those from the clinical sample from which they are derived. This casts some doubts as to whether the information gained by in vitro studies using these commercial cell lines accurately reflects the in vivo situation. Furthermore no normal ovarian epithelium-derived cell line, which could serve as control cells in ovarian cancer studies, are commercially available, although studies on the derivation and serial propagation of normal human ovarian surface epithelium in tissue culture have been described (Siemens et al., 1988, J. Cell Physiol. 134:347–351; Kruk et al. 1990, Lab. Inves. 63: 132–136). Importantly, no spontaneously established cell cultures from normal ovarian epithelium has been described, inunortalization being achieved through transfection with an oncogene (Wigler et al., 1978, Cell 14:725–731)

The derivation of histologically different and relatively pure cell cultures of ovarian origin would be extremely beneficial as they would provide a tool which would have a number of specific advantages over the starting clinical material and over the commercially available ovarian cell lines. The ability to propagate ovarian cancer cells in culture, free from contaminating normal cells, would provide a potent model to study ovarian cancer. In addition, the natural heterogeneity of ovarian cancer should be reflected more accurately by having access to a more diversified array of primary cultures of ovarian origin. Furthermore, a simple and rapid method to derive primary cultures from benign and malignant ovarian tissue and from ascites, should provide a model for patient-based research, such as drug screening studies. Such a patient-based model could be instrumental in orienting the cancer therapy of the patient thereby increasing the prognosis of the patient.

SUMMARY OF THE INVENTION

The present invention relates to established human ovarian surface epithelium cell line, derived from a normal or cancer cell of an ovarian surface epithelium clinical material, wherein the cell line is substantially equivalent to the cell of the clinical material from which it originates. These cell lines can serve as a powerful model:

a) to study the ovarian epithelium under normal and pathological conditions;

b) to assess the expression of specific genes involved in tumor suppression or tumor promotion;

c) for the screening of compounds that influence the level of expression of matrix metalloproteinase activity; and d) for the screening of compounds useful in human or animal medecine through their influence on tumorogenicity (using nude mice, for example), invasive potential, or on metalloproteinase activity.

The present invention also relates to immortalized cell lines derived from a clinical sample of ovarian cancer, the immortalization being carried out through successive passages in cultures, or through transfection with specific oncogenes.

The invention further relates to a simple and rapid method to derive primary cultures from benign and malignant ovarian tissue and from ascites from a patient with ovarian cancer. This method thus provides a model for patient-based research, that enables the clinician to test the response of the primary cell cultures to different types of treatment, thereby permitting a more precise design of an efficacious therapeutic regimen for cancer therapy.

In a preferred embodiment, the cell lines are spontaneously established cell lines of ovarian epithelium derived from normal tissue, malignant tumors and ascites. These cell lines are identified herein by the following designations: NOV31, for normal ovarian cell line; TOV21G and TOV112D for solid tumor-derived cell lines; and OV-90 for an extra-ovarian ascites cell line. These cell lines have been deposited on Oct. 19, 1994 with the American Type Culture Collection (ATCC), 12301 Park Lawn Drive, Rockville, Md. and cell lines NOV-31, TOV-21G, TOV-112D and OV-90 granted accession numbers CRL 11730, CRL 11731, CRL 11732 and CRL 11733, respectively.

The invention further relates to the use of these ovarian epithelium-derived cell lines to assess the expression of metalloproteinase inhibitors such as TIMP-1 and for the screening of pharmaceuticals that could potentiate or mimic the activity of genes involved in the regulation of metalloproteinase activity such as TIMP-1.

Since primary cultures can be established from different histological types and equally efficiently from all stages of ovarian cancer (including benign tumor) and compared to their normal counterparts in culture, the present invention provides a model to evaluate the temporal appearance and relative importance of specific molecular events in ovarian tumor progression.

In addition, the invention relates to the use of these ovarian epithelium-derived cell lines or primary cell cultures for the screening of compounds having anti-tumor activity, such as the non-cellular fraction of ascites, and to the use of the non-cellular fraction of ascites as an anti-tumor agent.

In particular, the invention relates to human primary ovarian surface epithelium cell culture, derived from a normal or cancer cell of an ovarian epithelium clinical material, the primary cell culture being substantially equivalent to the cell of the clinical material from which it originates.

Even more particularly, the invention relates to a method of screening for a compound that affects the tumorogenicity or invasive potential of a cell, comprising the steps of:

a) incubating one of cell lines NOV31 (ATCC, CRL 11730), TOV21G (ATCC, CRL 11731), TOV112D (ATCC, CRL 11732) or OV90 (ATCC, CRL 11733) with the compound for a sufficient number of cellular divisions to allow for an effect of the compound to be observed; and b) assaying the tumorogenicity or invasive potential of the treated cell line.

Moreover, the invention relates to a pharmaceutical or veterinary formulation for the treatment or the prevention of a disease involving at least one of tissue degradation, promotion of wound healing and tumor progression, comprising a non-cellular fraction of ovarian ascites and at least one of a pharmaceutically and veterinary acceptable carrier.

In the specifications and appended claims, it is to be understood that "metalloproteinase activity" is designed to include the level of RNA encoding the metalloproteinase and the level of metalloproteinase protein as well as the activity of the metalloproteinase per se.

The term "substantially equivalent" as used herein in the specification and appended claims, refers to the fact that the primary cultures of the present invention are representative of the cells from the clinical material from which they originate. The primary cultures of the present invention behave in a substantially equivalent ways to the cell from the clinical material from which they originate, at the morpholigical, physiological and molecular levels.

As used herein in the specification and claims, the term "tissue degradation" includes arthropathy, rheumatoid arthritis, inflammatory diseases such as osteoarthritis and gingivitis, dermatological diseases, corneal ulceration, diseases affecting bone resorption such as osteopenias, osteoporosis and periodontitis Other features and advantages of the invention will be apparent from the description of the preferred embodiments given hereinafter. However, it should be understood that the detailed description, while indicating preferred embodiments of the invention, are given by way of illustration only, since various changes and modifications within the spirit and scope of the invention will become apparent to those skilled in the art.

DETAILED DESCRIPTION OF THE INVENTION

Figure 1:
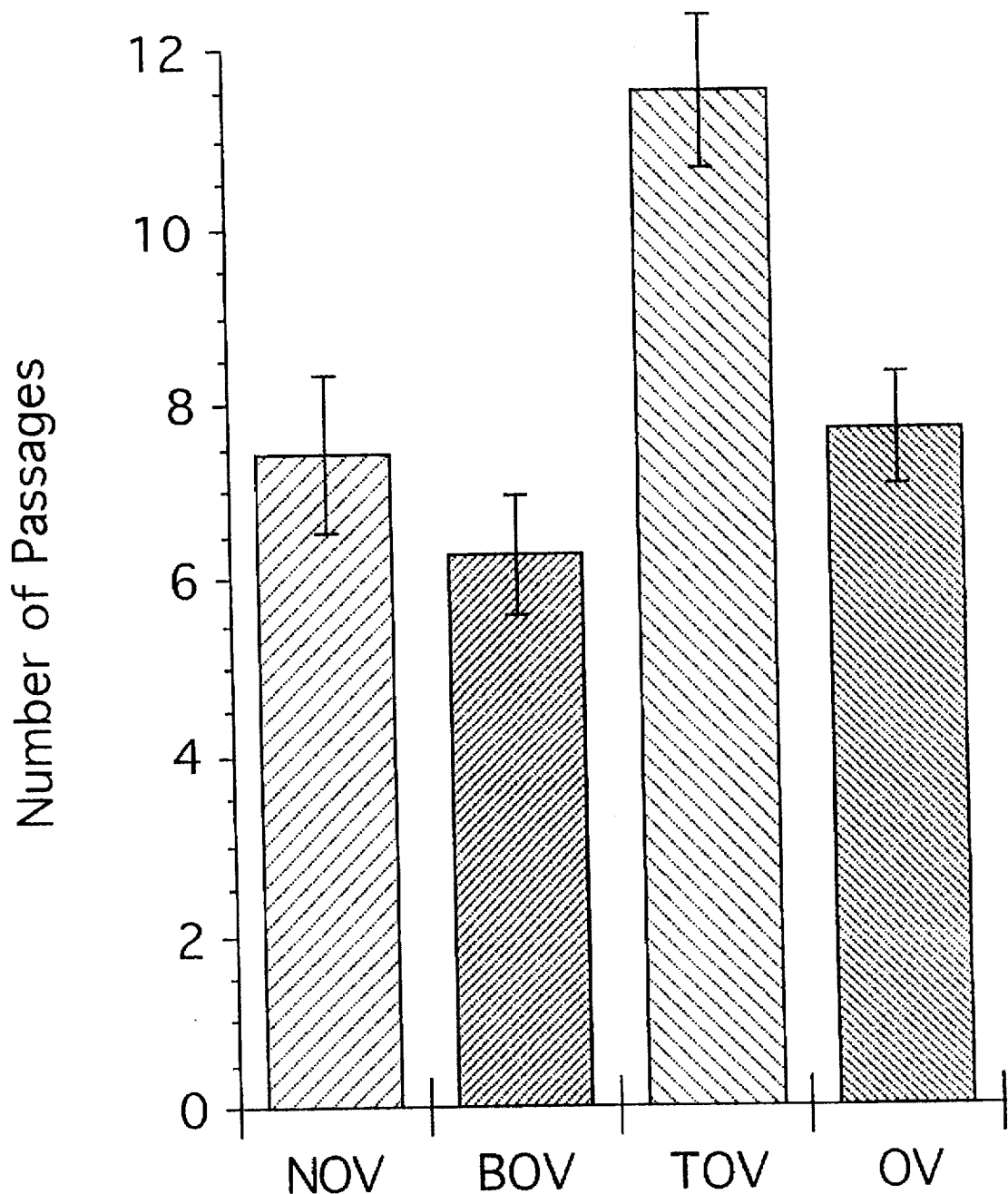
FIG. 1 depicts a Histogram showing the growth potential of primary cultures derived from normal ovary (NOV), benign tumor (BOV), malignant tumor (TOV) and ascitic fluid (OV)
Figure 2A:
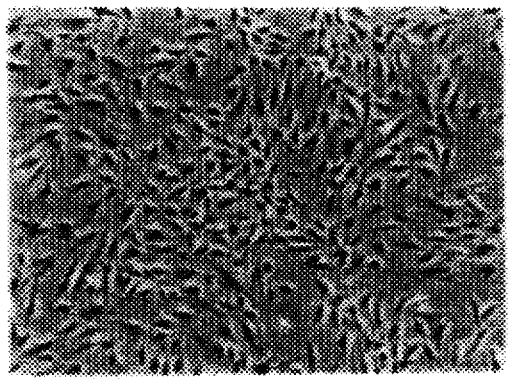
FIG. 2A–D shows morphological aspects and growth pattern of primary cultures derived from: (A) NOV; (B) BOV; (C) TOV; and (D) OV primary cell cultures.
Figure 2B:
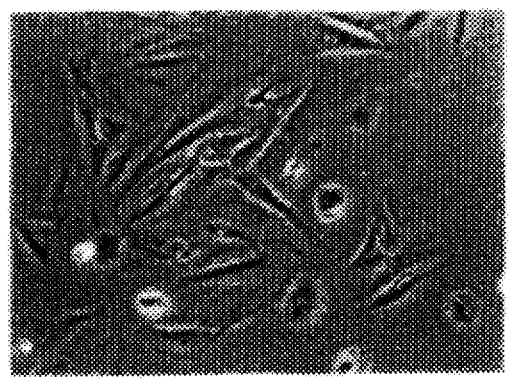
Figure 2C:
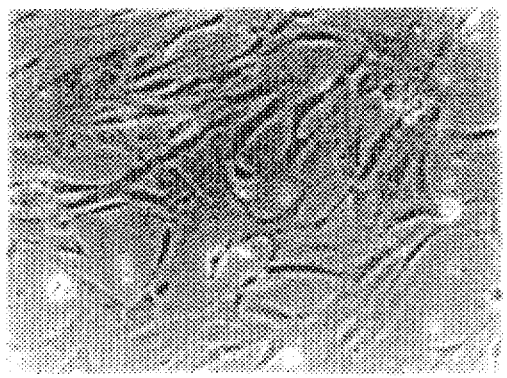
Figure 2D:
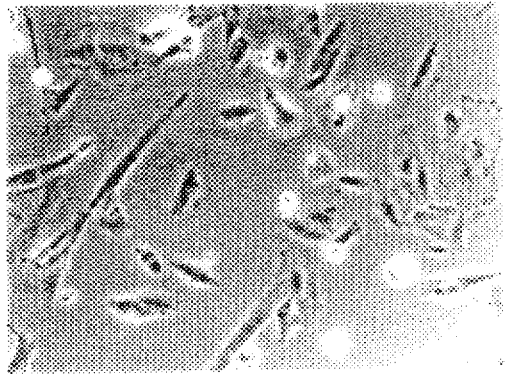

In the absence of a suitable model system for the study of ovarian cancer, clinical samples were used to derive OSE cultures from normal ovaries, malignant ovarian tissue and ascites. The derivation of relatively pure cell cultures which represented the cells in the original clinical material was one of the main goals of the present invention.

I. DEVELOPMENT OF PRIMARY CULTURES

Fresh material from ovarian tumor and normal ovaries were collected during laparotomies performed at the Hôpital Notre-Dame, Montréal. All specimens were collected aseptically. In the case of ovarian tumors (either benign or malignant) preliminary pathological examination were performed and representative sections were transported to the laboratory on ice. Histological reports were subsequently obtained, and tumors were graded and staged according to the International Federation of Gynecology and Obstetrics criteria. A portion of each sample was snap frozen and stored in liquid nitrogen, a portion was used to extract DNA, and the remainder was used to derive primary cultures. In the case of ascites, specimen were obtained either at the time of laparotomies or from therapeutic paracentesis. The cellular fraction was collected by centrifugation and stored at $-80°$ C. in 90% FBS:10% buffered DMSO solution (50 ml DMSO, 3.03 gm Tris-base, 1.25 gm dextrose, 1.68 gm sodium citrate, $H_2O$ to 100 ml, pH 6.7).

Normal OSE cultures were obtained by the scrape method (Kruk et al. 1990, Lab. Inves. 63: 132–136). Cultures from normal ovaries were maintained in OSE media consisting of 50:50 medium 199:105 (Sigma) supplemented with 15% FBS (Kruk et al. 1990, Lab. Inves. 63: 132–136). The OSE media was consistently supplemented with 2.5 ug/ml FUN-GIZONE™ and 50 ug/ml gentamicin.

To establish cultures from solid tumors (benign and malignant), tissues were minced with scissors into 2–4 mm explants in OSE media (without FBS). Enzymatic dissociation was accomplished by digestion with 1,000 units of collagenase for 4 to 12 hours (h). The best results were obtained when a 1:4 ratio of pure (Sigma: C-9407) to crude (Sigma: C-9891) collagenase was added. Addition of even small quantities of trypsin (1:1,000 dilution of a 0.05% solution) resulted in a greatly diminished plating efficiency. After the collagenase treatment, aggregates were dissociated by gently pipetting and the remaining undigested solid material was allowed to sediment and was discarded. The cellular fraction was diluted 1:5 in OSE media supplemented with 10% FBS, placed in 100 mm dishes (Nunc), and incubated undisturbed at 37° C. in 5% $CO_2$/air for 24–48 h. After cells had adhered to the plastic they were washed once in PBS (136 mM NaCl, 2.6 mM KCl, 6.6 mM $Na_2HPO_4$, 1.5 mM $KH_2PO_4$ pH 7.4).

For ascites, the cellular fraction was collected by centrifugation. When ascites contained contaminating red blood cells, the pelleted cellular fraction was incubated with mild agitation at 37° C. in 25 ml of a lysis solution (10 mM Tris pH 8.0, 1.44 mM $NH_4Cl$). Unlysed cells were subsequently collected by centrifugation. Cell pellets devoid of red blood cells were resuspended in 10 ml of OSE media with 10% FBS per $10^6$ cells and plated on 100 mm plastic dishes. Cells were allowed to adhere at 37° C. in 5% $CO_2$/air for 24 h. Because of the substantial debris in these cultures, cells were washed twice in PBS the following day.

Subsequently, cultures were regularly fed every three to four days and subcultured by a 1:2–3 split ratio by detaching cells after one PBS wash with 1 ml of trypsin solution from Gibco (0.05% Trypsin and 0.53 mM EDTA in Hank's balanced salt solution without calcium and magnesium). When possible, early passage and late passage primary cultures were frozen in buffered DMSO freezing solution.

For the growth of OSE-derived cells from benign or malignant ovarian neoplasias, similar conditions to the optimized conditions described by Kruck et al. 1990 (Lab. Inves. 63: 132–136) were used. Indeed, in preliminary experiments, it was clear that OSE media was superior to conventional media (RPMI 1640 and Dulbecco's modification of Eagle's Media) in the support of cell growth. In addition, no significant differences were observed when comparing different types of plastic for either the initial establishment or the subsequent passage of primary cultures. While fresh biopsy samples were the optimum choice as a starting material, the scheduling of operations sometimes precluded the immediate processing of some samples. It was noted that if samples were kept on ice overnight, cultures could still be established, albeit at a reduced success rate.

Primary cell cultures were derived from normal ovary (NOV), benign tumors (BOV), malignant tumors (TOV) and ascites from ovary (OV). NOV, BOV, TOV and OV cultures were established in culture at frequencies of 51%, 45%, 66% and 56% respectively. A portion of early passage cultures were frozen and these cells were easily reestablished in culture in greater than 80% of cases. The average number of passages for which the various primary cultures could be maintained in vitro was evaluated and is shown in FIG. 1. BOV cultures were generally more difficult to maintain and could only be passaged on average 6 times. In contrast, TOV cultures generally grew well and were maintained an average of 11–12 passages. NOV and OV cultures averaged 7–8 passages. However, rare NOV, OV and TOV were spontaneously immortalized and have been maintained for over 30 passages. One TOV line (TOV21G) which was established early-on has been maintained in culture for greater than 70 passages.

II. CHARACTERIZATION OF PRIMARY CULTURES

Morphological characterization

Of utmost importance was to determine whether the cells in culture were representative of the epithelial cells from the original tumor. It has previously been shown that epithelial cells maintained in OSE media preserve their epithelial morphology (Kruk et al. 1990, Lab. Inves. 63: 132–136). Thus cultures were evaluated for the presence of epithelial versus atypical/fibroblastic contamination.

Figure 3A:
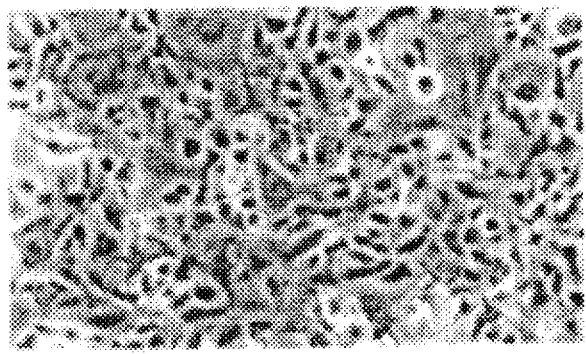
FIG. 3A–C shows the similar morphology between immortalized cell lines: (A) TOV21D, established from a grade III malignant adenocarcinoma of the ovary; (B) OV90, derived from a malignant ovarian ascites; and (C) commercially available NIHOVCAR3, a cell line derived from a malignant ovarian ascites.
Figure 3B:
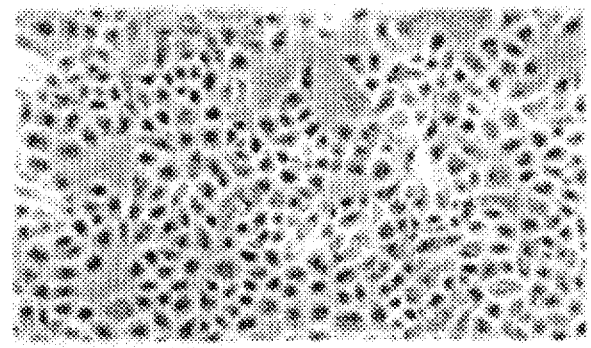
Figure 3C:
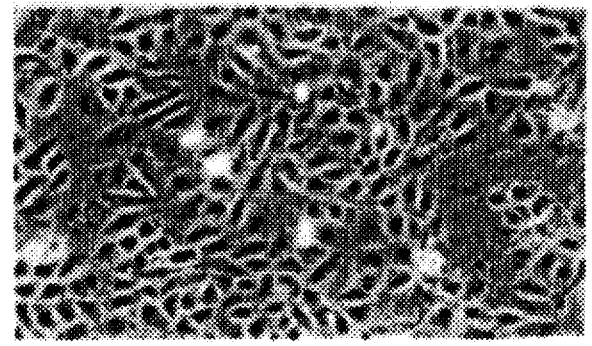

Morphological examination of cultures revealed that the major cellular component of the cultures where epithelial-like (FIG. 2). NOV cultures were highly homogeneous and morphologically indistinguishable from cultures described in (Kruk et al. 1990, Lab. Inves. 63: 132–136). BOV and OV cultures were also very homogeneous, while in TOV cultures variable levels of fibroblast-like cells were often observed, although the latter quickly disappeared after two-three passages. In BOV cultures, cells were characteristically large with abundant cytoplasms while in OV and TOV cultures cells were generally smaller and cellular outer membranes had a characteristic ruffled appearance (FIG. 2). Spontaneous immortalized TOV and OV cultures had a different appearance which more closely resembled the morphology of the NIHOVCAR-3 (FIG. 3) which was spontaneously derived from a malignant ascites.

To address whether the cells in culture were truly epithelial in origin, immunofluorescence studies using an antibody directed against the epithelial-specific cytokeratins were performed. Briefly, cells were grown on 8 chamber LAB-TEK SLIDES™ (Nunc) in OSE media supplement with 10% FBS. Slides were washed twice in PBS, fixed by incubation in 2:1 acetone:methanol at −20° C. and air dried for 30 min at room temperature. Slides were blocked in 10% FBS/PBS for 30 min at room temperature. Anti-cytokeratin antibody (AE1/AE3 monoclonal anti-epithelial keratin mix, ICN) was diluted 1:50 in PBS and incubated Immuno 30 min at 37° C. Immunodetection was subsequently performed using a streptavidin:biotin fluorescein based kit (ICN). Nuclei were counterstained with ethidium bromide (1 mg/ml) for 15 min Slides were washed in PBS, air dried and mounted with PERMOUNT™ (Sigma).

NOV cultures showed well-organized keratin filaments while cells from OV, TOV and BOV cultures showed a more diffuse but positive staining with anti-cytokeratin antibodies, a staining pattern typical of transformed epithelial cells.

Molecular characterization

The pattern of chromosome 3 deletions and p53 mutations in primary culture was analyzed as they bear directly on the question of the relationship between the primary cells in culture and the neoplastic cells of the original tumor. RFLP analysis of chromosome 3 deletions was used to detected loss of heterozygocity (LOH) at specific regions of chromosome 3.

DNA used in a number of different analysis was extracted using standard protocols (Sambrook et al., 1989, In Molecular Cloning, Cold Spring Harbor Laboratories Press). Restriction fragment length polymorphism (RFLP) was analyzed using a combined PCR/RFLP technique (Ganly et al., 1991, Nucleic Acids Res. 19: 3757; id: 3760; Ganly et al., 1992, Genomics 12: 221–228) Briefly, primers were used to amplify a portion of genomic DNA which contains the HindIII polymorphism associated with the pBH302 probe mapped to human chromosome 3p24 (Gareau et al., 1988, Nucleic Acids Res. 16: 1223; and see Example 1). An other set of primers were used to amplify a portion of genomic DNA which contains the MspI polymorphism associated with D3S30 marker mapped on 3p14 (Gareau et al., 1988, Nucleic Acids Res. 16: 1223; and see Example 1). PCR and digestion product were resolved on 2% agarose TBE gels.

Single-strand conformation polymorphism (SSCP) analysis was performed (Orita et al., 1989, Genomics 5: 874–879). Samples were subjected to 2 rounds of PCR. First, exons 5 through 9 were amplified for 33 cycles and each sample was purified on a G-25™ column and ethanol precipitated. DNA was resuspended in 20 µl, diluted 1:100 and 2 µl of this mixture was used to amplified exon 5 (5'-TATCTGTTCACTTGTGCCCTCAC-3' and 5'-CCACTCGGATAAGATGCTGAGGA-3') and exon 7 (5'-AAGGCGCACTGGCCTCATC-3' and 5'-AGTGTGCAGGGTGGCAAGTGG-3') separately. Reaction conditions were similar to the first amplification except that the PCR mixture contained 5 µCi of [$\gamma^{32}$P] dCTP (3000 Ci mmol$^{-1}$). For SSCP analysis, the PCR product was diluted 3-fold in 0.1% SDS, 10 mM EDTA and 5 µl was added to 15 µl of sequencing stop solution (95% formamide, 10 mM EDTA, 0.05% bromophenol blue, 0.05% xylene cyanol), heat denatured at 95° C. for 3 min, chilled on ice and 5 µl was loaded onto a non-denaturing polyacrylamide gels (49:1 acrylamide to bis-acrylamide). Following electrophoresis, gels were dried and exposed to X-ray film at −80° C. for one or two days.

In a subset of samples, DNA from both the original specimen and cells in culture was obtained. In 37 informative samples, eleven (11) were shown to have suffered deletions in chromosome 3 while the remainder were intact for the two regions tested. Significantly, there was 100% correlation between the results from tumor DNA and DNA isolated from the cells in culture.

Similarly, p53 mutations were detected by SSCP analysis. While mutations in p53 were infrequent, the appearance of the same p53 mutation in tumor DNA and DNA isolated from the matched cells in culture was observed. In particular, mutant SSCP patterns were observed in exon 7 from a TOV sample and in exon 5 from an OV sample. In both cases, the DNA from the original tumor displayed the corresponding mutant pattern as well as varying degrees of the wild-type SSCP pattern. This wild-type pattern in the original tumor DNA is presumably due to normal cell contamination, since in the TOV and OV samples, mutations in one allele of p53 were accompanied by loss of the second allele through chromosome deletion. Sequence analysis of p53 mutations revealed the identical point mutation in the tumor and corresponding cellular sample. Thus, a large body of evidence supports the concept that the cells in culture are truly representative of the epithelial cancer cells in the original tumor.

In summary, primary cultures derived from normal ovary or from ovarian tumors and ascites were established from approximately 50% of the clinical samples obtained. These, primary cultures could be maintained for a significant number of passages in vitro.

These cultures were extensively characterized by a number of evaluation criteria. By all criteria used, the cells in culture seem to be derived, and are substantially equivalent to the cancer cells in the original tumor. The early passages of TOV and BOV cultures contained however, a variable number of contaminating fibroblast-like cells, as evidenced by SSCP analysis of early versus late passage cultures of the exon 7 mutated TOV culture. These results, as well as the morphological observations, suggest that, initially, cultures derived from solid tumors may contain varying amount of contaminating normal cells but that this contamination resolves itself over the life span of the culture.

The cells of the ovarian cell lines of the present invention (NOV-31 (CRL 11730), TOV-21G (CRL 11731), TOV-112D (CRL 11732) and OV-90 (CRL 11733), provide numerous advantages over the commercially available ovarian cell lines. Among them, the disclosed normal ovarian cell line is the first ovarian cell line having been immortalized spontaneously, without transfection of an exogenous oncogene. NOV-31 can be used in numerous studies related to embryogenesis, hormone regulation, cell senescence and pathogenic condition, including the initiation and progression of tumor formation. Furthermore, NOV-31 can be used a substrate to test the role of different genes in ovarian tumor progression. The ovarian tumor cell lines and ascites (TOV21G, TOV112D and OV90) can be used advantageously in numerous studies including the assessment of molecular events associated with ovarian tumor progression, including the mapping of new suppressor genes or oncogenes. The ovarian cancer cell cultures of the present invention can further be used to test the activity of candidate suppressor genes or of compounds affecting their invasive potential, such as the non-cellular fraction of ascites, and can be immortalized by transfection with oncogenes.

The cell lines of the present invention also retain the traditional advantages of cell lines, such as permitting to study their local microenvironment for importance in autocrine, paracrine or juxtacrine events in cell proliferation, growth and differentiation. They obviously can serve as sources for genetic material (DNA) or of gene products (mRNA, and protein) which can lead to the identification of defects responsible for the disease (i.e.: mutation in a suppressing gene such as p53 or increased expression of an oncogene such as neu). They can be used in therapeutic assays such as chemosensitivity or chemoresistance, or in growth modulation studies, such as the effect of retinoic acid.

The method of deriving primary cultures of the present invention provides pure cell cultures, free of necrotic material that could falsify the results of experiments. The primary cell cultures of the invention further reflect the clinical heterogeneity of ovarian cancer and permit cellular and molecular analyses and are substrates for genetic manipulation. They can be used to identify molecular defects that can be correlated with the patient's outcome, thereby having a profound impact at the clinical level. For example, by correlating a molecular defect (high expression of an oncogene, or the mutation of a tumor suppressor gene) with a specific pattern of disease progression, molecular defects responsible for clinical manifestations of the ovarian cancer can be identified. The method of deriving primary ovarian cancer cells provides the assessment of a personalized tumor profile for a given patient. This personalized tumor profile can be immensely useful to clinicians as it will provide a chemosensitivity pattern and invasive potential of the tumor cells thereby permitting the identification of the suitable chemotherapeutic agents or other modes of intervention efficacious for the treatment of the disease. The invasive potential of the patient's cells can be assessed by a number of ways including the Matrigel™ assay. Studies as to the modulation of this invasive potential through the use of pharmaceuticals, the modulation of TIMP or the addition of ascites fluid can also be performed. The metalloproteinases being involved in tissue degradation, wound healing and the like, results on the modulation of TIMP can be applied to a variety of diseases including rheumatoid arthritis. The primary cell cultures can further be used or modified as mentioned above for the established cultures of the invention.

EXAMPLE 1

Analysis of genetic abnormalities associated with ovarian cancer

The genetic events involved in human ovarian cancer development are still largely unknown although numerous karyotype analyses have demonstrated a number of recurrent chromosomal abnormalities. The presence of these chromosomal rearrangements may point to the disruption of tumor suppressor genes whose normal role would be to regulate cell growth or alternatively, to the activation of tumor promoting genes.

The karyotypes of solid tumors are often complex with chromosomal deletions being difficult to detect. More recently, chromosomal deletions have been identified by loss of heterozygosity (LOH) at polymorphic loci. This method has shown that chromosomal deletions are much more common than had been identified cytogenetically. More detailed analysis of chromosomal arms with several polymorphic markers can thus be used to identify a common region of deletion associated with a specific cancer, and allow the localization of a tumor suppressor gene within a small region of the chromosome.

LOH studies have been used to demonstrate that deletion within the short arm of chromosome 3 commonly occur in many different cancers. Ovarian cancer is also characterized by non-random deletions in the short arm of chromosome 3. LOH was most closely associated with probes specific for the 3p24 region (Ehlen and Dubeau 1990, Oncogene 5: 219–223; Zheng et al., 1991, Cancer Res. 51: 4045–4051) and this loss has been correlated to the more aggressive disease (Zheng et al., 1991, Cancer Res. 51: 4045–4051).

The primary cultures of the present invention were used to detect and map chromosome 3p deletions. Using genomic DNA purified from these cultures PCR/RFLP analysis was performed to assess the condition of chromosome 3 by a previously described technique (Ganly et al., 1992, Genomics 12: 221–228). PCR reactions were performed on genomic DNA sequences which spanned a polymorphic site recognized by a restriction enzyme in regions 3p14 and 3p21 of chromosome 3. More particularly, primers were used to amplify a portion of genomic DNA which contains the HindIII polymorphism associated with the pBH302 probe (Gareau et al., 1988, Nucleic Acids Res. 16: 1223) mapped to human chromosome 3p24. The sense primer sequence was 5'-ACGTTAGTGGCTCATATGAC-3' and antisense 5'-TCATTCGAGTTAGTGCAAAG-3'. If the HindIII site is present, the 432 bp PCR fragment is cleaved into 221 and 211-bp fragments. MspI and DraI polymorphisms from 3p24 were also identified using the sense primer 5'-AACGTTGGACCTCAAGCCCAT-3' and antisense primer 5'-CAGGGTTCCTTCTATAAACATG-3'. Primers 5'-AAAGACTTCCTTCTGAGATGGG-3' and 5'-CAGTCTGCTGTGGTTTCAGTCT-3' were also used to amplify a portion of genomic DNA which contains the MspI polymorphism associated with D3S30 marker mapped on 3p14. If the MspI site is present, the 293-bp PCR fragment is cleaved into 224 and 69-bp fragments. PCR amplification was performed in a volume of 20 µl containing 0.5 µg of genomic DNA, 0.2 µM of each primer, 1.25 mM of each dNTP, 1.5 mM MgCl$_2$, 50 mM KCl 10 mM Tris (pH 9.0) 0.001% gelatin, 1% Triton X100® and 0.5 units Taq polymerase (Pharmacia). A total of 30 cycles were carried out, each cycle consisting of denaturing at 95° C. for 0.5 min, annealing at 55° C. for 1 min, and extending at 72° C. for 1 min Extension during the final cycle was continued for 5 min The entire PCR product was then digested overnight in a volume of 50 µl with 10 units of the appropriate restriction enzyme. The digests were size fractionated on 2% agarose gel and stained with ethidium bromide (Sambrook et al., 989, In Molecular Cloning, Cold Spring Harbor Laboratories Press).

Homozygous and heterozygous individuals for the various regions were identified. In heterozygous individuals, chromosome 3 loss was scored as positive in tumor samples no longer displaying the heterozygous pattern.

Figure 4:
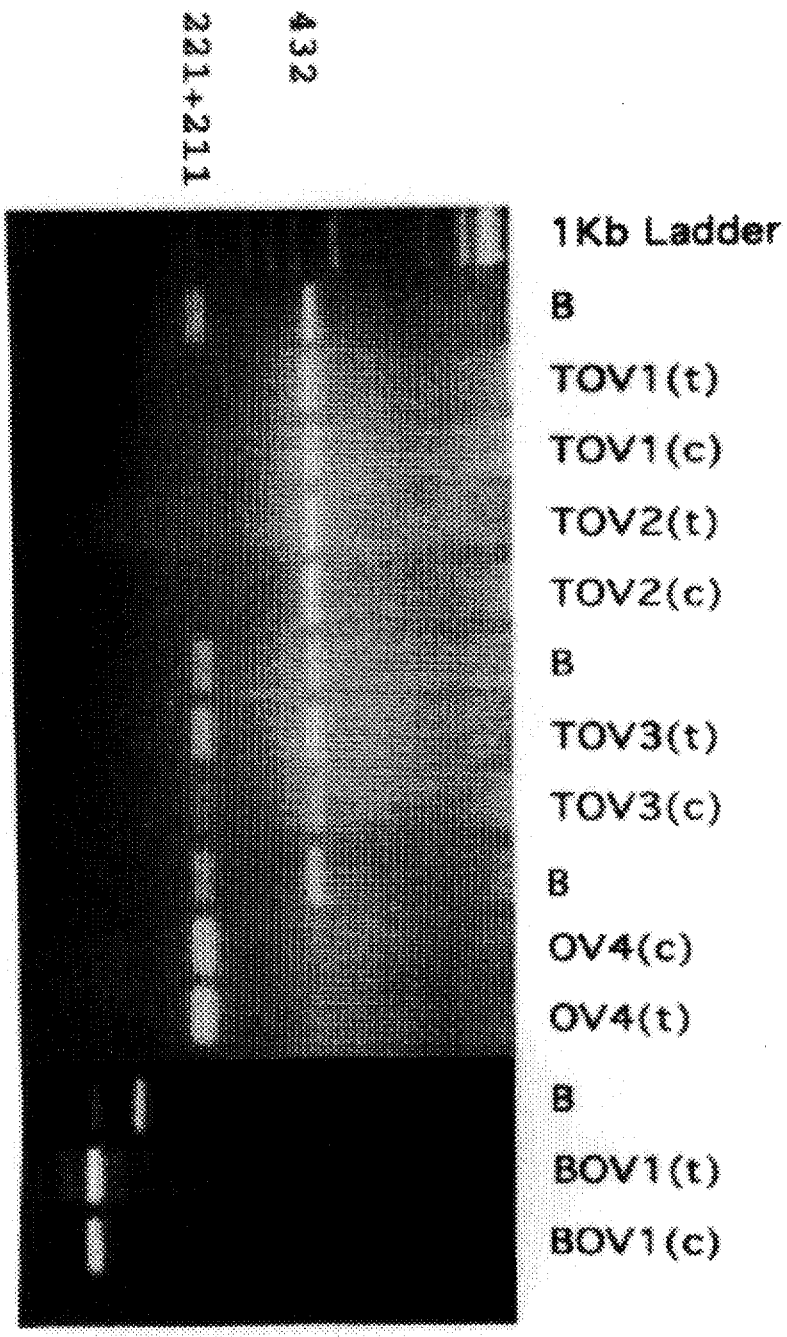
FIG. 4 shows a comparison of RFLP patterns seen in fresh clinical ovarian samples and in the corresponding primary cell cultures. The first 11 lanes show a digestion with HindIII of the polymorphic region in THRβ locus (3p24) amplified by PCR. S: matched blood DNA. The last three lanes are from a separate experiment and contain samples analyzed by RFLP/PCR and MspI digestion for the D3S30(3p14) locus.
Figure 5:
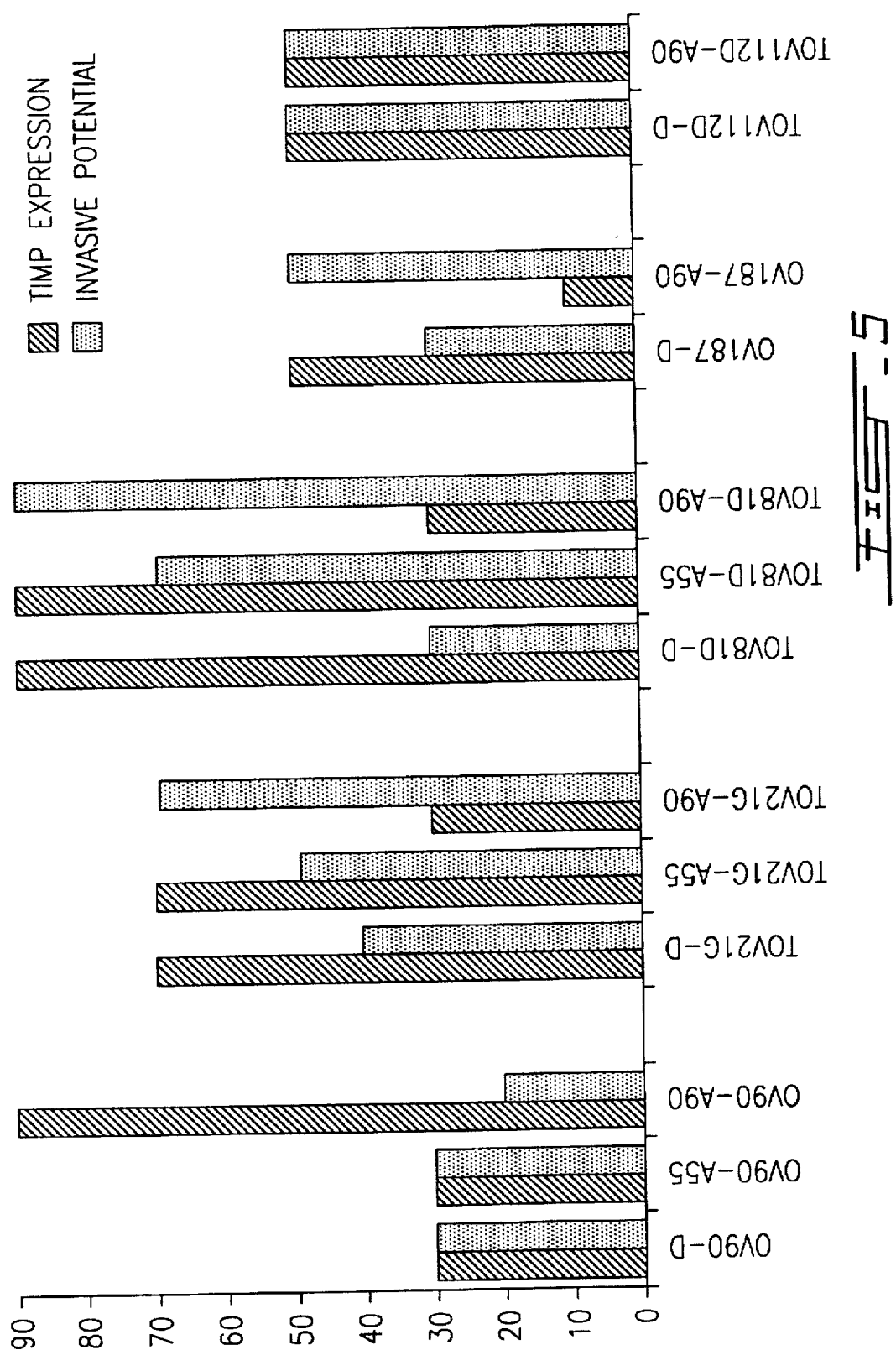
FIG. 5 shows the correlation between the level of TIMP expression in cells and their invasive potential.

A representative example of PCR/RFLP analysis at the THRβ locus (3p24) is presented in FIG. 4. Blood samples SO37 and tumor sample OV37 both display a heterozygous pattern indicating that these two alleles of chromosome 3are intact. In contrast, while the STOV21 is also heterozygous, in this case the primary culture TOV21D and TOV21G (which represent samples from the left and right ovary from the same patient) have clearly lost one of the two alleles. The LOH was also analyzed with other primers for THRβ. Using the three polymorphic markers at the THRβ locus, it was observed that out of 43 samples tested, 35 were informative for at least one of the polymorphic markers. The LOH at D3S30 (3p14) with oligonucleotide primers D3S1 and D3S2 was also examined. The results of these analyses, which also include the original tumor histology, are summarized in Table 1. Finally, all samples displayed LOH for both original tumors and matched primary cultures (including TOV, OV and BOV samples) indicating a 100% correlation between the PCR/RFLP patterns from primary cells in cultures and the corresponding original tumors. Thus, the primary cultures of the present invention are truly representative of the original clinical sample from which they are derived and can be used to study the genetic events associated with ovarian cancer.

TABLE 1

Loss of heterozygocity for chromosome 3P

| Specimen | Histology | Grade | LOH 3P24 | LOH 3P14 |
|---|---|---|---|---|
| TOV-21G | adenocarcinoma | III | LOH | R |
| TOV-21D | adenocarcinoma | III | LOH | R |
| TOV-76 | adenocarcinoma | ND | LOH | — |
| TOV-20 | adenocarcinoma | ND | R | — |
| TOV-81 | adenocarcinoma | I | R | — |
| TOV-55G | adenocarcinoma | — | R | — |
| TOV-123D | adenocarcinoma | II | R | R |
| TOV-112D | adenocarcinoma | III | R | R |
| TOV-9 | adenocarcinoma | III | — | R |
| OV-37 | adenocarcinoma | ND | R | — |
| OV-36 | adenocarcinoma | 0 | LOH | LOH |
| OV-38 | adenocarcinoma | ND | LOH | — |
| OV-22 | adenocarcinoma | ND | LOH | — |
| OV-90 | adenocarcinoma | III | LOH | — |
| OV-55 | adenocarcinoma | III | R | — |
| OV-128 | adenocarcinoma | ND | — | R |
| OV-33 | adenocarcinoma | III | LOH | — |
| TOV-101 | adenocarcinoma | I | — | R |
| TOV-83D | adenocarcinoma | III | R | — |
| OV-30 | adenocarcinoma | ND | LOH | — |
| TOV-128 | adenocarcinoma | I-II | — | R |
| OV-123 | adenocarcinoma | II | R | R |
| TOV-123G | adenocarcinoma | II | — | R |
| TOV-103G | adenocarcinoma | I | R | R |
| TOV-170 | adenocarcinoma | III | R | R |
| OV-156 | adenocarcinoma | II | R | — |
| OV-147 | adenocarcinoma | III | R | — |
| OV-159 | adenocarcinoma | III | R | — |
| OV-171 | adenocarcinoma | II | — | R |
| TOV-88 | adenocarcinoma | ND | R | — |
| NOV-16 | normal | — | R | — |
| NOV-17D | normal | — | R | — |
| NCV-15 | normal | — | R | — |
| NOV-27 | normal | — | R | — |
| NOV-26G | normal | — | R | — |
| NOV-107G | normal | — | R | — |
| NOV-121D | normal | — | — | — |
| NOV-80G | normal | — | R | — |
| BOV-96G | serous cyst | — | — | R |
| BCV-122D | benign | — | R | — |
| BOV-38G | serous cystadenoma | — | — | LOH |
| BOV-53 | fibroma | — | R | — |
| BOV-108D | benign | — | R | — |

ND: no data, R: retention

EXAMPLE 2

Expression of candidate suppressor genes associated with ovarian cancer

The primary ovarian cultures of the present invention provide a unique system in which to assess the expression of specific genes. This type of analysis, using epidermoid-tumor-derived cell lines, was instrumental in elucidating the suppressor potential of RARβ in epidermoid lung cancer (Houle et al., 1991, Genes, Chromosomes and Cancer 3: 358–366). Because chromosome 3p deletions occur frequently in ovarian cancer, the pattern of expression of three candidate suppressor genes which map to 3p has been determined.

RNA analysis

Total RNA was extracted from growing cells by the guanidium isothiocyanate-cesium chloride procedure (Sambrook et al., 1989, In Molecular Cloning, Cold Spring Harbor Laboratories Press). Gene expression was analyzed with the RNase protection assay. Probes were generated from plasmids by in vitro transcription with the T7 polymerase (Pharmacia) and then precipitated with 20 µg of total RNA of the sample to be analyzed. Pellets were resuspended in 30 µl of hybridization mix, heated at 85° C. for 5 min and incubated at 50° C. for 16 h. RNase digestion buffer (300 µl) containing 2 µg/ml of RNaseT1 and 80 µg of RNase A was then added, and the mixture was incubated at 36° C. for 1 h. 20 µl of 10% SDS and 50 µg of proteinase K were added, followed by a 15 min incubation at 37° C. Samples were then extracted with phenol chloroform-isoamyl alcohol (25:24:1), precipitated, resuspended in denaturing loading buffer, and run on a 6% polyacrylamide/8M urea denaturing gel. The templates used to generate the RNA probes were: i) pBH2, carrying a 310-bp BglII-HindIII fragment from pBLRARβ, cloned in the BamHI-HindIII sites of pGEM-2; ii) perbAβSac, carrying a 345-bp fragment from THRβ cDNA, cloned in the pT7-T3 18 vector; and iii) pBH11 carrying a 309-bp BamHI-SacI fragment of the human β-actin gene containing 212-bp of exon 3 and 87-bp of intron 3 (Houle et al., 1991, Genes, Chromosomes and Cancer 3: 358–366). Prior to transcription perbAβSac and pBH11 were linearized with HindIII while pBH-2 was digested with AvaI.

Reverse transcription-PCR analysis

Gene expression was studied with reverse transcription (RT) of mRNA by the combined RT-PCR technique. First strand cDNA synthesis was carried out on 5 µg of total cellular RNA using 100 units of Moloney murine leukemia virus reverse transcriptase after priming with 18 ng random hexamer primers in buffer containing 10 mM Tris pH 8.6, 1.5 mM MgCl$_2$, 0.01 gelatin and 37 units of RNase GUARD™ (Pharmacia). The reactions were incubated at 42° C. for 1 h. A volume of 3 µl of cDNA product was used for the PCR amplification with a set of specific primers. Amplification was performed in 50 µl of reaction mixture containing 1 µM of each primer 0.5 mM of each dNTP, 1.5 mM MgCl$_2$, 0.01% gelatin , 10 mM Tris pH 8.6, 50 mM KCl and 0.5 units of Taq polymerase. The reactions were performed as follows: 94° C. for 3 min followed by five cycles of 93° C. for 1 min , 50° C. for 40 sec and 70° C. for 1 min followed by 25 cycles of 93° C. for 1 min 45° C. for 30 sec and 70° C. for 5 min Twenty µl of the PCR product were analyzed on 1.5% agarose gel (Pharmacia). Oligonucleotide primers used were pgh1 5'-CTTTACCAGGAAAAGACTCTA-3' and pgh2 5'-TGCTGTCTATTAAACTATAGG-3' for PTPase γ (Krueger et al., 1990, EMBO J. 9: 3241-3252), and VH1 5'-CACAGCTACCGAGGTCACCTT-3' and VH2 5'-ATACTTCTCTAATGGGCAGGC-3' for the VHL candidate suppressor gene (Latif et al., 1993, Science 260: 1317–1320).

While THRβ has not been shown to be a suppressor gene, its expression was verified since LOH often affects this gene. In the case of THRβ and RARβ, the sensitive RNAse protection assay was used to assess RNA levels in primary cultures. THRβ and RARβ were weakly expressed in all samples tested, including RNA purified from NOV, OV, BOV, and TOV derived cultures. In addition, this weak expression was unaffected in samples displaying LOH at the THRβ locus. Characterization of the different RARβ isoforms in these primary cultures using an RT-PCR assay showed that all samples tested (including NOV, TOV, BOV, OV samples) expressed the β2 and β4 isoforms of RARβ.

In tumor cell lines from lung cancer, RARβ expression is undetectable (Houle et al., 1991, Genes, Chromosomes and Cancer 3: 358–366). In contrast, no decrease in the level of RARβ was observed in ovarian tumor-derived cultures as compared to normal ovarian epithelial cultures. In addition, the pattern of isoform expression was identical in all samples.

RT-PCR technique was also used to look at the RNA pattern for the PTPaseγ (3p21) and VHL candidate suppressor gene (3p25). It revealed that both PTPaseγ and the VHL candidate suppressor are expressed in all epithelial cell lines, whether derived from normal ovary or from ovarian tumors. These assays, though not quantitative, do indicate that both PTPaseγ and the VHL candidate suppressor are expressed at some level in these primary cultures. Uniform expression of the VHL candidate gene was seen in all primary cultures, including three NOV, four BOV, five TOV and five OV samples. In contrast, loss of PTPaseγ expression was observed in a non-epithelial ovarian cancer.

Thus, the primary ovarian cultures of the present invention provide a unique system in which to assess the expression of specific genes. This type of analysis, using epidermoid-tumor-derived cell lines, was instrumental in elucidating the suppressor potential of RARβ in epidermoid lung cancer (Houle et al., 1991, Genes, Chromosomes and Cancer 3: 358–366). These primary ovarian cultures could thus be useful in identifying genes implicated in ovarian cancer.

EXAMPLE 3

Expression of a matrix metalloproteinase (MMP) inhibitor, TIMP-1

Because actual treatment modalities of ovarian cancers often fail, it is important to understand the biological parameters which affect tumor spread and growth in order to eventually identify new targets for therapeutic interventions. Metastases have been correlated with decreased levels of TIMP expression and published results strongly suggest that reduced transcription of the TIMP gene under conditions of serum depletion can be the cause of increased proteolytic activity in metastatic cell lines (Ponton et al., 1991, Cancer Res. 51: 2138–2143). Furthermore, given the role of MMPs in a number of disease states, there is considerable interest in the therapeutic potential of MMP inhibitors.

In an attempt to investigate the role of TIMP regulation in ovarian cancer, the levels of TIMP RNA in the primary cultures of the present invention were analyzed. RNA was extracted from cells following growth under normal culture conditions (10% FBS) or in serum-depleted media (0.1% FBS) for 48 h. In some cases serum-depleted media was supplemented with 100 μl of the non-cellular fraction of ascites. The latter was prepared by filtration of an ovarian ascites through a Nalgene 0.45 μm filter and the filtrate stored at −20° C. The same ascites preparation was used in all experiments.

Total RNAs were prepared from both primary cultures and cell lines by the guanidium/CsCl procedure (Sambrook et al., 1989, In Molecular Cloning, Cold Spring Harbor Laboratories Press). The quality of the purified RNA was determined spectrophotometrically and by examination of a small quantity after agarose gel electrophoresis and ethidium bromide staining.

10 μg of total RNA from cells derived from ovarian cultures were electrophoresed in a 1% agarose gel containing 2.2M formaldehyde and 20 mM MOPS (3-[N-morpholine] propane sulfonic acid, pH 6.8). RNA was transferred to nitrocellulose membrane (Schleicher & Schuell) by capillarity blotting with 20×SSC (1×SSC is 0.15M NaCl/0.015M sodium citrate, pH 7.0) and baked at 80° C. for 2 h. The filters were hybridized overnight at 60° C. in 30% formamide/0.35M sodium phosphate, pH 7.2, 7% SDS, 1% bovine serum albumin with a random primed [$\alpha^{32}$-P] dCTP-labeled linearized plasmid containing the murine TIMP coding sequences. Filters were subsequently washed twice at 60° C. with 0.15 sodium phosphate, 1% SDS. Autoradiograms were exposed to Kodak XAR-5™ film for two to five days at −70° C. with an intensifying screen. As a control, filters where re-hybridized with [$\alpha^{32}$-P] dCTP-labeled plasmid containing the mouse β-actin sequences and treated as previously described.

The results of the TIMP mRNA levels in the different primary cultures is shown in Table 2. Four different NOV primary cultures were tested. Three of the NOV cultures displayed moderate to high level of TIMP mRNA, and the level of expression was independent of the growth conditions. Only NOV-26G gave different results, and in this culture, TIMP expression was high in serum starved conditions and low in normal growth conditions. This NOV-26G culture is unusual in that cells were maintained for over 15 passages before crisis.

Primary cultures derived from solid ovarian tumors, whether benign or malignant (benign [BOV], and malignant [TOV]), show moderate to high levels of TIMP mRNA both in serum-starved and normal growth conditions. TOV-21G is of particular interest because this primary culture has been maintained over 70 passages and is considered to be immortal.

Three ovarian ascites primary cultures have evaluated and in all cases, the same pattern of expression was observed Table 2. Under normal growth conditions, only low to undetectable levels of TIMP mRNA are observed while serum-depleted cultures retain high TIMP mRNA expression. Surprisingly, addition of the non-cellular fraction of ascites in serum depleted conditions resulted in a further increase in TIMP mRNA levels.

Analysis of two commercially available cell lines derived from malignant ovarian ascites (NIHOVCAR-3 and SKOV-3) showed a pattern of expression different from that of the primary OV cultures of the present invention. In particular, TIMP expression was constitutively low and no serum responsiveness was observed.

TABLE 2

Level of TIMP mRNA in primary cultures

| Source of material | culture | level TIMP mRNA under normal growth conditions | level TIMP mRNA under serum-depleted conditions | level TIMP mRNA under serum-depletion with ascites fluid |
|---|---|---|---|---|
| Normal ovaries | NOV - 26G | (+) | (+++) | |
| | NOV31 | (++) | (++) | |
| | NOV-61 | (+++) | (+++) | |
| | NOV-131 | (++) | (++) | |
| Benign ovarian tumors | TOV-28/B* | (+) | (+) | |
| | BOV96G | (+++) | (+++) | |
| | BOV-122D | (+++) | (+++) | |
| Malignant ovarian tumors | TOV21G | (++) | (++) | |
| | TOV55G | (++) | (++) | |
| | BOV81D/T* | (+) | (+) | |
| | TOV112 | (+++) | (+++) | |
| | BOV103G/T* | (+++) | (+++) | |
| | TOV128D | (+) | (+) | |
| | TOV159 | (+++) | (+++) | |
| Ovarian ascites | OV-90 | (+) | (+++) | (+++++) |
| | OV-123 | (++) | (+++) | (+++++) |
| | OV170 | | (++) | (+++++) |
| Other: | | | | |
| colon ascites | | (+) | (+++) | (+++++) |
| colon tumor | | (+++) | (+) | |
| ovarian cell line | NIHOVCAR3 | (−/+) | (−/+) | |
| | SKOV3 | (−/+) | (−/+) | |
| | SW626 | (−/+) | (−/+) | |

In summary, using the model system of the present invention it was shown that in cultures derived from solid tumors (either benign or malignant) transcription of TIMP is constitutively moderate to high and does not depend on the presence of serum. In contrast, cell cultures from fresh ascites give a completely different profile. In these cells basal levels of TIMP expression in serum starved conditions is high, and they decrease sharply in response to serum stimulation. In addition, and very importantly, it has been demonstrated that the non-cellular fraction of ascites acts as a potent stimulator of TIMP expression in serum depleted conditions. These results would suggest that cells in ascites have limited proteolytic potential, and may help to explain their growth without solid support. The non-cellular fraction of ascites could therefore be used as potent anti-tumor agent.

In contrast, the NIHOVCAR-3 and SKOV-3 cell lines do not demonstrate the same pattern of serum responsiveness as the primary ovarian cultures. This result may either indicate fundamental differences between cells within the malignant tumor which are capable of establishing immortal cultures or may reflect alterations in TIMP patterns of expression related to continued passage in tissue culture. If the latter is true, this would highlight the importance of studies done in primary cultures, as these may more closely reflect the situation in vivo.

Finally, it has been documented that, in patients with ascites, the disappearance of ascites, either through drainage or following chemotherapy is often followed by relapse with multiple solid tumors. This clinical pattern correlates well with the observation that the non-cellular fraction of ascites increases TIMP expression. Thus, the disappearance of ascites in a patient would be accompanied by a decrease in TIMP expression in tumor cells, which would allow these cells to adhere to solid support, providing a focus for further solid tumor growth.

Numerous methods of correlating the invasive or tumorogenic potential of cells with the metalloproteinase activity can be used. For example, the total metalloproteinase activity of cells can be monitored by using zymogrammes (Unemori et al., 1986, J. Cell. Biol. 103: 1021–1031; and Ponton et al., 1991, Cancer Res. 51:2138–2143).

EXAMPLE 4

Determination of the invasive potential of cells using the Matrigel™ assay

Matrigel™ (Collaborative Biomedical Products Becton Dickinson Labware) derived from EHS sarcoma (murine tumor from the connective tissue which is naturally rich in membranes proteins) one assay which permits the identification of the invasive potential of cells. The major components of the Matrigel™ dish are the following: laminin, collagen 4, proteoglycans (heparin sulfate), entactin and growth factors. The invasion chambers are constituted of membrane having 8 microns pores, the membrane being coded by a layer of Matrigel™ matrix. This matrix blocks the pores of the membrane thereby inhibiting the crossing of noninvasive cells.

On day one of the Matrigel™ assay, 1 ml of OSE media (with 10% FBS) is added to the wells and placed at 4° C. for 24 hours. The cells for which the invasive potential is to be tested are starved by growing in a depleted OSE medium (Gentamicin, FUNGIZONE™ and 0.1% FBS) for 48 hours. 1 ml of the depleted OSE media is then added to the Matrigel™ chambers in order to create a FBS gradiant, thereby favoring a migration of the cells toward the highest FBS concentration, and therefore from the Matrigel™ chamber through the matrix coated membrane and into the well. The dish is placed at 4° C. for 24 hours. The cells which had been growing in the OSE depleted media are trypsinized and resuspended in depleted OSE media and their concentration adjusted to 15,000 cells/ml. 1 ml of the cell suspension is transferred to Matrigel™ chamber of the dish which is then placed at 37° C. for 2 days. The cells ware then fixed on the exterior side of the Matrigel™ membrane so as to only fix the invasive cells. Fixation is carried at −20°

C. for 2 hours using methanol. Cells were subsequently stained with a Giemsa 10% solution (10% Giemsa and 90% PBS) for 48 hours. The Matrigel™ chambers were washed with water and the cells counted under the microscope.

For the assessment of the action of the cell free fraction of ascites on the different cellular types, the complete OSE medium as well as the depleted OSE medium present in the wells was replaced by depleted OSE medium containing 0.1% ascites. Seven (7) cellular types were tested in the Matrigel™ assay:

OV-90:. ascites of an ovarian neoplasia;

TOV-21G: neoplasia of the left ovary;

TOV-81D: neoplasia of the right ovary, serous papillary, grade I;

TOV-112D: primary ovary neoplasia, adeno-carcinoma;

OV-187: malignant ovarian ascites;

NOV-61: ovarian presenting typical cells with a benign aspect; and

NOV-31: normal ovarian epithelium.

The invasive potential of the cells is categorized in five (5) classes reflecting the percentage of cells that have crossed the Matrigel™ (i.e. 0 to 20%).

Table 3 shows the invasive potential of the above mentioned cells, under three (3) types of conditions: in OSE depleted media, in the presence of a non-cellular fraction of ascites OV-55 (A-55) and in the presence of the non-cellular fraction of ascites OV-90 (A-90).

The numbers in Table 3 represent the absolute number of cells having crossed the Matrigel™ membrane, following a 48 hours incubation. As can be seen, all cells, including normal cells have an invasive potential, although their degree of invasiveness varies upon the cell type in the culture conditions. The invasive potential of NOV-31 can be explained by the activity of the normal ovarian epithelial cells in tissue remodeling. As evidenced by Table 3, invasive potential of a primary cell culture isolated from a patient can be assessed. It follows that the assay could also be performed in the presence of numerous types of compounds in order to test their activity on the invasive potential of the cell studied.

Table 3 also shows the effect of the noncellular fraction of ascites and more particularly, its role in potentiating the invasive potential of TOV-81D. It is noteworthy, that while OV-90 appears non responsive to the non-cellular fraction ascites A-55, its invasive potential is decreased by the addition of its own non-cellular fraction ascites (A90). Thus once again the potential of the non-cellular fraction of ascites as an anti-tumor agent is shown. Performing the same type of assays on further purified fractions of the non-cellular fraction of ascites can lead to the identification of the active component responsible for tumor suppression.

TABLE 3

| CELL TYPE | DEPLETED | | A-55 | | A-90 | |
|---|---|---|---|---|---|---|
| OV-90 | 125/111 | (++) | 122 | (++) | 79/61 | (++/+) |
| TOV-21G | 161/145 | (++/+++) | 180 | (+++) | 202/262 | (++++) |
| TOV-81D | 110 | (++) | 217 | (++++) | 325 | (+++++) |
| OV-187 | 73 | (++) | | | 145 | (+++) |
| TOV-112D | 173 | (+++) | | | 169 | (+++) |

TABLE 3-continued

| CELL TYPE | DEPLETED | | A-55 | A-90 | |
|---|---|---|---|---|---|
| NOV-61 | 47 | (+) | | 183 | (+++) |
| NOV-31 | 148 | (+++) | | 164 | (+++) |

Legend: (100% = 330 cells)
0 " 20%: +
20 " 40%: ++
20 " 60%: +++
60 " 80%: ++++
00 " 100%: +++++

EXAMPLE 5

Transfection of cells with an oncogene

A modification of the calcium phosphate technique (Wigler et al., 1978, Cell 14: 725–731) was used to transfect NOV-14 cells with CsCl density gradient purified supercoiled plasmid DNA. NOV-14 cells were plated on 100 mm plastic dishes at a cell density of 7×10cells/plate, and were incubated for 48 hours in DMEM supplemented with 10% FBS. The medium was then changed and 4 hours later the DNA calcium phosphate precipitate was added. The precipitate was prepared as follows. One drop of 2M $CaCl_2$ was added to 3.375 ml of $H_2O$. To this was added, drop by drop, 1 ml of water containing DNA (200 ug total, consisting of the desired amount of recombinant plasmid DNA with the balance being made up of calf thymus DNA). Additional 2M $CaCl_2$ was added drop by drop until the final volume of 2M $CaCl_2$ added was 630 ul. The entire solution was vortexed. This solution was gently bubbled into a tube containing 5 ml of 2×HBS pH 7.1 (50 mM Hepes, 280 mM NaCl) and 0.1 ml of 0.07M $Na_2HPO_4$. The resulting precipitate was allowed to form for 30–45 minutes at room temperature. One ml of the precipitate was added per plate by directly pipetting it onto the medium. The precipitate remained on the plates for 2–3 hours after which the cells were washed in 10 ml of PBS, and new medium was added. After 48 hours, cells were placed under G418 selection (120 ug/ml) and the medium was routinely changed three days after, until foci were ready to be picked (3–4 weeks post transfection). It is noteworthy that numerous attempts using a commercial lipofecting kit were generally unsuccessful as only a single clone (NOV-70G-1) could be obtained. Furthermore, $CaPO_4$ was shown to be highly toxic to ovarian primary cells, since all experiments wherein the precipitate was left for more than 5 hours resulted in cell death.

A multitude of plasmids and oncogenes can be used for immortalizing the cell cultures of the invention. For example, BAP PyLT, having a β-actin promoter driving the expression of polyomavirus large T-antigen expression or BAP SV40tsA having a α-actin promoter driving the expression of an SV40 temperature sensitive mutant of the large T-antigen.

While the invention has been described with particular reference to the illustrated embodiment, it will be understood that numerous modifications thereto will appear to those skilled in the art. Accordingly, the above description and accompanying drawings should be taken as illustrative of the invention and not in a limiting sense.

We claim:

1. An established cell line obtained from a clinical sample of human ovarian epithelium, wherein said established cell line behaves in substantially equivalent ways at the morphological, physiological and molecule levels to a cell from said clinical sample from which said established cell line originates, and wherein said cell is a non-cancerous cell and said established cell line has all of the identifying characteristics of a cell line selected from the group consisting of TOV-21G, TOV-112D and OV-90 having a ATCC accession number CRL 11730, CRL 11731 and CRL 11732, respectively.

2. The established cell line of claim 1 immortalized by transfection with an oncogene.

3. The established cell line of claim 1, wherein said cell line is selected from the group consisting of TOV-21G, TOV-112D and OV-90 having ATCC accession number CRL 11730, CRL 11731 and CRL 11732, respectively.

4. The established cell line of claim 3 immortalized by transfection with an oncogene.

5. An established cell line obtained from a clinical sample of human ovarian epithelium, wherein said established cell line behaves in substantially equivalent ways at the morphological, physiological and molecular levels to a cell from said clinical sample from which said established cell line originates, and wherein said cell is a non-cancerous cell and said established cell line has all the identifying characteristics of NOV-31, having ATCC accession number CRL 11733.

6. The established cell line of claim 5 immortalized by transfection with an oncogene.

7. The established cell line of claim 5, wherein said cell line is NOV-31, having ATCC accession number CRL 11733.

8. The established cell line of claim 7 immortalized by transfection with an oncogene.

* * * * *